(12) United States Patent
Leeming et al.

(10) Patent No.: US 7,576,244 B2
(45) Date of Patent: Aug. 18, 2009

(54) COMPOUNDS AND COMPOSITIONS FOR USE AS FOAMING OR FROTHING AGENTS IN ORE AND COAL FLOTATION

(75) Inventors: Philip Joseph Leeming, Mereweather Heights (AU); Stewart John Knight, New Lambton Heights (AU); Salvatore Lazzaro, Taylors Lakes (AU); Jeffrey Roy Aston, Taylors Lakes (AU); David Hayshiv Parris, Parkville (AU)

(73) Assignee: Huntsman Corporation Australia Pty. Limited, West Footscray, Victoria (AU)

( * ) Notice: Subject to any disclaimer, the term of this patent is extended or adjusted under 35 U.S.C. 154(b) by 352 days.

(21) Appl. No.: 10/538,249

(22) PCT Filed: Dec. 9, 2003
(Under 37 CFR 1.47)

(86) PCT No.: PCT/AU03/01646

§ 371 (c)(1),
(2), (4) Date: Apr. 13, 2006

(87) PCT Pub. No.: WO2004/052815

PCT Pub. Date: Jun. 24, 2004

(65) Prior Publication Data

US 2006/0239876 A1    Oct. 26, 2006

(30) Foreign Application Priority Data

Dec. 9, 2002    (AU) ............... 2002953252

(51) Int. Cl.
*C07C 43/11* (2006.01)
*B03D 1/012* (2006.01)
*C01G 3/00* (2006.01)

(52) U.S. Cl. ............... 568/679; 568/618; 568/622; 252/61; 209/166; 423/26

(58) Field of Classification Search ............... None
See application file for complete search history.

(56) References Cited

U.S. PATENT DOCUMENTS

| | | | |
|---|---|---|---|
| 4,582,596 A | 4/1986 | Hansen et al. | 209/166 |
| 5,753,738 A | 5/1998 | Chapman et al. | 524/376 |
| 5,844,115 A * | 12/1998 | Moody et al. | 568/618 |
| 5,855,769 A * | 1/1999 | Firth et al. | 209/164 |
| 6,051,057 A | 4/2000 | Yatake et al. | 106/31.58 |
| 2002/0157568 A1 | 10/2002 | Adachi et al. | 106/31.58 |

FOREIGN PATENT DOCUMENTS

| | | |
|---|---|---|
| CA | 1336520 | 8/1995 |
| EP | 0 186 815 A1 | 7/1986 |
| EP | 0 506 087 A2 | 9/1992 |
| GB | 1 388 012 | 3/1975 |
| WO | WO 97/35095 | 9/1997 |
| WO | WO 01/92439 A1 | 12/2001 |

OTHER PUBLICATIONS

Satoru et al. (computer generated English language translation and English abstract of JP 2001-131107, published May 2001).*
Klimpel (Some results of various new chemical reagents for modifying coal flotation performance, Coal Preparation, 1992, 10(104), abstract).*
CAPLUS Database Accession No. 2001:347078, May 15, 2001.
CAPLUS Database Accession No. 2000:465157, Jul. 11, 2000.
CAPLUS Database Accession No. 1999:719493, 1999.
CAPLUS Database Accession No. 1986:34041, 1985.
CAPLUS Database Accession No. 1970:476349, 1970.
CAPLUS Database Accession No. 1954:79233, 1954.
CAPLUS Database Accession No. 1988:548882, Dec. 16, 1987.
CAPLUS Database Accession No. 1995:663193, Apr. 4, 1995.
Beilstein Database Accession No. 2073498, 1962.
Ashburn, H., et al., "β-Amoxyethyl Esters of ρ-Aminobenzoic Acid," *J. Am. Chem. Soc.*, 58:1549-1551, Sep. 1936.
Blomberg, C., et al., "Internal Reactions in the Grignard-Complex Containing Compounds with Alkoxy-groups. Part II. Cyclic Acetals," *Recueil*, 82:355-360, 1963.
Aldrich Catalogue Handbook of Fine Chemicals 1994-1995, "2-Isopropoxyethanol," catalogue No. 10, 789-1, p. 844.

* cited by examiner

*Primary Examiner*—Rosalynd Keys
(74) *Attorney, Agent, or Firm*—Ron D. Brown; Edward Korompai

(57) ABSTRACT

Compounds of formula (I) wherein $R_1$ and $R_2$ are each independently $C_1$-$C_2$ alkyl, and m is 1, 2, 3, 4, or 5 and compositions of formula (II) wherein $R_1$ and $R_2$ are each independently $C_1$-$C_4$ alkyl, and n is an integer $\geq 0$ and wherein the average molar value of n for the total of the compounds of formula (II) in said composition is in the range of (1) to (3) and methods for production thereof.

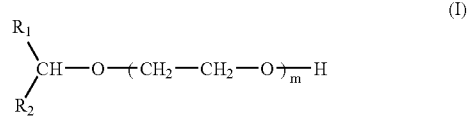

(I)

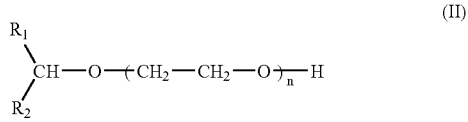

(II)

29 Claims, No Drawings

COMPOUNDS AND COMPOSITIONS FOR USE AS FOAMING OR FROTHING AGENTS IN ORE AND COAL FLOTATION

CROSS-REFERENCE TO RELATED APPLICATIONS

This application is a U.S. National Phase Application of International Application No. PCT/AU2003/001646, filed Dec. 9, 2003, which claims priority to Australian Patent Application No. 2002953252, filed Dec. 9, 2002. Both of these applications are incorporated herein by reference in their entireties.

FIELD OF THE INVENTION

The invention relates to novel compounds and compositions and to methods for their preparation. The compounds and compositions of the present invention find particular application as foaming or frothing agents in ore and coal flotation processes, as well as in other industrial processes involving froth flotation. The compounds and compositions may also find applicability as surfactants in hydraulic fluids.

BACKGROUND OF THE INVENTION

Froth flotation is a widely used process for separating fine solids from other solids by taking advantage of the disparity in wetability at solid particle-surfaces. Separation of a solid mixture may be accomplished by the selective attachment of hydrophobic solid particles to gas bubbles. Most often the gas used is air, which is generally passed through a liquid mixture of the crude solids at such a rate as to provide a sustained "froth" or accumulation of bubbles at the liquid-surface interface. The density difference between the gas bubbles and liquid provides the attached solid particles with buoyancy, lifting the hydrophobic solid particles to the surface and leaving behind non-hydrophobic solids in the bulk liquid mixture. The hydrophobic solid particles at the surface remain attached to the surface froth and can be subsequently separated from the bulk mixture by draining the bulk mixture or mechanically skimming the surface froth.

In froth flotation a frothing or foaming agent is added to stabilise the bubbles which carry the hydrophobic solid particles to the surface. The stabilisation of the bubbles or surface froth greatly enhances the separating efficiency of the unwetted hydrophobic particles from the bulk liquid-solid mixture. The frothing agent or "frother" acts by stabilising the bubbles through the lowering of the liquid surface tension enhancing the performance of dissolved air froth flotation processes. "Stabilisation" in relation to flotation refers to both the increased lifetime of the bubbles and the increased bubble surface area generated by lowering the average bubble size.

Froth flotation techniques have been used in the mining industry for around 150 years. Many different minerals and non-minerals are processed using froth flotation. These include for example silver, nickel, zinc, titanium, cobalt, and chromium (metals) as well as quartz and kaolinite (non-metals). Today, mining companies are finding it more and more difficult to find high grades of ore. Accordingly, there is a growing demand to provide more effective separation processes to balance the ever increasing economical burden which mining companies face as they process poorer grades of ore. As such, improvements in froth flotation techniques would be of much benefit to the present day mining industry.

Froth flotation has also been used in other industries including the chemical industry. It is also used in sewage and water treatment applications. Examples include the separation of organic contaminants and oil from water streams, de-inking of used newsprint and magazine furnishes in the paper industry as described for example in U.S. Pat. No. 6,544,383 amongst many others, as well as the separation of plastics and so on.

A major user of froth flotation is the coal industry for desulfurisation and for the recovery of "clean coal". Clean coal is required by end users who set defined specifications for the coal that they purchase. These will usually include maximum limits on ash or "non combustible" matter in the form of clays, gypsum and other minerals, as well as the maximum sulphur content in order to minimise discharge of environmentally unfriendly $SO_x$ gases upon combustion of the coal. The process of producing "clean coal" is often referred to as "beneficiation" or coal washing. In coal washing, the mined coal is crushed and slurried in water. A collector, typically a kerosene or diesel hydrocarbon fraction and a frother are added to the slurry and the mixture passed through conventional flotation cells or devices where the fuel rich material is separated from the ash or fuel poor material.

Specially designed flotation devices include for example a Jameson® Cell, Microcel®, and EKOF® cells. Jameson® cells are extensively used in the beneficiation of coal.

A good frother must possess a number of key properties. Different frothers will be better suited to different applications, however, in general terms, a frother must be able to promote the formation of stable air bubbles under aerated conditions. Frothers are typically comprised of both polar and non polar components. The non polar or hydrophobic moiety will orient itself into the air phase while the polar or hydrophilic component will tend to the liquid (usually water) phase. The result is an enhanced bubble wall strength and stability due to localised increase in surface tension. This will enhance the ability of the bubbles to hold and concentrate the desired mineral.

Effective frothers usually contain at least 5 carbon atoms in a straight chain or branched configuration which provide the hydrophobic interaction with the air phase and a polar group which is typically a hydroxyl (—OH) functionality. The balance of these two functionalities will determine the effectiveness of a particular frother for a particular application. Typical frothers currently in use in the mining industry include aliphatic alcohols like 2-ethyl-3-hexanol, cyclic alcohols (for example, pine oil), 1,1,3-triethoxybutane, and polyalkylene glycols.

One of the most commonly used all purpose flotation frothers for coal, base metal and other non-metal flotation is 4-methyl-2-pentanol, commonly known as "MIBC" (methyl isobutylcarbinol). MIBC has long been the reagent of choice in flotation applications which use Jameson® cells.

MIBC displays excellent surface behaviour, solubility and has been widely adopted in the industry due to its relatively low cost and good froth generation performance, especially in applications where the minerals are relatively hydrophobic and readily floatable. However, MIBC is highly flammable displaying a Pensky-Martens closed cup flash point of 41° C. (106° F.). MIBC also omits an unpleasant odour and accordingly is not very pleasant to work with. MIBC is classified as a dangerous good according to the National Standard for the Storage and Handling of Workplace Dangerous Goods [NOHSC; 1015(2001)] and the National Code of Practice: Storage and Handling of Workplace Dangerous Goods [NOHSC: 2017(2001)] and accordingly, requires special care when handled, transported or stored in large volumes. Consequently, this compound poses a substantial occupational, health and safety (OH&S) concern. It is apparent from this that a need exists for a less volatile alternative to MIBC, that has better flammability and odour characteristics and is generally safer to deal with in general use.

SUMMARY OF THE INVENTION

It has now been surprisingly found that $C_3$-$C_9$ secondary alcohols having a low degree of ethoxylation have the ability to act as effective frothers, and also have the added advantage of possessing higher flash points over the parent alcohols, making them less flammable and less volatile. These compounds also display better odour characteristics than the parent alcohols.

Accordingly, in one aspect the present invention provides compounds of the formula (I):

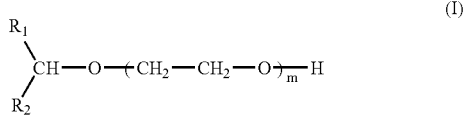

wherein $R_1$ and $R_2$ are each independently $C_1$-$C_4$ alkyl, and m is 1, 2, 3, 4, or 5.

In another aspect the invention provides a composition comprising at least two compounds of the formula (II):

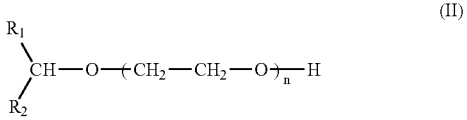

wherein $R_1$ and $R_2$ are each independently $C_1$-$C_4$ alkyl, and n is an integer $\geq 0$ and wherein the average molar value of n for the total of the compounds of formula (II) in said composition is in the range of 1 to 3.

In yet another aspect, the present invention provides a method for preparing a composition comprising at least two compounds of formula (II):

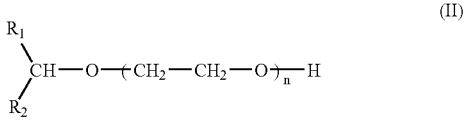

wherein $R_1$ and $R_2$ are each independently $C_1$-$C_4$ alkyl, and n is an integer $\geq 0$, and wherein the average molar value of n for the total of the compounds of formula (II) in said composition is in the range of 1 to 3, said method comprising;

reacting an excess of $C_3$-$C_9$ secondary alcohol with ethylene oxide in the presence of a catalyst in an ethoxylation vessel to form a mixture of two or more compounds of formula (II), separating at least a portion of unreacted secondary alcohol from the mixture, and recycling unreacted secondary alcohol back into the ethoxylation vessel.

The term $C_1$-$C_4$ alkyl group refers to straight chain or branched alkyl groups of from 1 to 4 carbon atoms. Examples of suitable alkyl groups include methyl, ethyl, n-propyl, cyclopropyl, isopropyl, n-butyl, iso-butyl, tert-butyl and cyclobutyl. Preferably the group $R_1R_2CH$— is selected from the group consisting of pent-4-yl, pent-2-yl, pent-3-yl, 2-methyl-pent-3-yl, 4-methyl-pent-2-yl, hex-2-yl, hex-3-yl.

Most preferably the group $R_1R_2CH$— is 4-methyl-pent-2-yl.

The $R_1R_2CH$— group together with the O atom in the compounds of formula (I) can be derived from a $C_3$-$C_9$ secondary alcohol. Accordingly, the group $R_1R_2CHO$— represents the residue of a $C_3$-$C_9$ secondary alcohol. As such, the compound of formula (I) according to the present invention may be prepared by ethoxylating a secondary alcohol with ethylene oxide (EO). It will be recognised that m in formula (I) refers to the number of molecules of EO which have added per molecule of the secondary parent alcohol.

It will be understood that $R_1$ and $R_2$ may independently represent different $C_1$-$C_4$ alkyl groups or the same $C_1$-$C_4$ alkyl group.

The most preferred compounds of the present invention are those in which m is 1-5. More preferable are those compounds in which m is 1-3.

Preferred compounds of formula (I) are those which exhibit a closed cup flash point of greater than or equal to 61° C. Most preferred compounds of formula (I) are those which exhibit a closed cup flash point of greater than 65° C. In the description which follows (including the examples) the quoted flash points of the compounds and compositions of the present invention are measured using a Pensky-Marten flashpoint apparatus, using standard methods such as AS/NZS 2106.2 which is identical with ISO 2719.

Primary alcohols generally react much faster than secondary alcohols during ethoxylation with EO. Because of the disparity in reaction rates between primary and secondary alcohols there is a tendency for EO to react with secondary alcohols which have already been ethoxylated, than to react with a molecule of an unreacted parent secondary alcohol. Accordingly, the product mixtures of such reactions will invariably contain mixtures of ethoxylated, multi-ethoxylated and non-ethoxylated secondary alcohols. Surprisingly, it has now been found that compositions of such mixed products comprising at least two compounds of formula (II) are also effective frothing agents exhibiting beneficial properties.

With specific reference to the compositions of the parent invention the term "average molar value of n" refers to the combined molar average of ethoxylated compounds of formula (II) which are present in the compositions of the present invention. For the present invention the average molar value of n is in the range of 1 to 3, and more preferably 1 to 2 and most preferably about 1.7.

It will be understood that n refers to the number of ethylene oxide molecules which have been substituted per molecule of $C_3$-$C_9$ secondary alcohol. In the present invention n is an integer greater than or equal to 0. As such, the compositions of the present invention may comprise non-ethoxylated products (n=0), mono-ethoxylated products (n=1) and multi-ethoxylated products (n>1). Therefore, the compositions of the present invention may comprise a mixture of mono-ethoxylated and non-ethoxylated products, mono-ethoxylated and multi-ethoxylated products, multi-ethoxylated and non-ethoxylated products or a combination of mono, non, and multi-ethoxylated products, wherein the average molar value of n of the composition is in the range of 1 to 3.

It is generally thought that ethoxylation of alcohols will greatly alter their properties in relation to those of the parent alcohol. Unexpectedly, it has been found that the compositions of the present invention display surface behaviour which is very similar to that of the parent alcohol. The additional advantage of the compounds and compositions of the present invention is that their flash point is raised relative to the parent alcohol without losing the characteristics which make for a good frother.

The flash points of the compositions of the present invention can be controlled to a desired level by varying the amount of n=1 (monoethoxylate product), and/or n=0 (parent alcohol or non-ethoxylated product) in the composition. Although maintaining good frothing qualities these compounds (n=1 or 0) tend to have lower flash points with respect to the same compounds which have undergone multiple ethoxylation (ie., where n>1). As a result, the compositions of the present invention display the same beneficial properties which the parent alcohol displays including the formation of a dry brittle and effervescent froth, and similar froth stability. However, the composition of the present invention are superior frothers in comparison with the parent $C_3$ to $C_9$ alcohols as they have the added advantage of higher flash points, and accordingly are less volatile.

The compositions of the present invention may have an amount of unreacted parent $C_3$-$C_9$ secondary alcohol (ie, where n is 0) that is less than 15% by weight of the total composition. It is preferred that the composition contain no more than 10% of the parent alcohol. More preferably however, the compositions of the present invention contain no more than 8% of the parent alcohol, for instance, less than or equal to 6.5% by weight of the total composition.

It is also a preferred feature that the compounds of formula (II) where n is greater than 4 account for less than 20% by weight of the total composition.

The present invention has been developed for the purposes described herein. The composition may be blended with a number of other products in its final use dependant on the requirements of the application. These include but are not limited to other frothers (eg alcohol or glycol type), collectors (eg kerosene and diesel), dispersants, depressants, neutralising agents (such as acetic acid, and the like), water or other solvents. Accordingly, in the case of frothing applications, the present invention provides a frother or frothing composition comprising a compound or composition as described above in combination with one or more additives selected from frothers, collectors, dispersants, depressants, neutralising agents and solvents. In such frothers one of the component, for example water, may act in more than one capacity, for example as flash point modifier and a solvent. The invention also provides surfactants, hydraulic fluids, dyes, oils and resins incorporating a compound or composition as described above together with other suitable additives.

The method of obtaining the desired compositions can be achieved through restricting the degree of ethoxylation of the secondary alcohol and then removing the compounds where (n=0 and/or n=1) from the composition mixture in a single distillation. A person skilled in the art would understand that the degree to which ethoxylation of the compounds of formula (I) can be restricted will be dependent upon the catalyst and reaction conditions used. Primarily, a lower degree of ethoxylation can be achieved by reacting an amount of secondary alcohol which is in a molar excess with respect to the amount of EO. Preferably the ratio of EO to secondary alcohol is kept below 70 wt %. More preferably the ratio is below 12 wt %, for instance, below 10 wt %. In this manner the excess parent alcohol can be distilled, recycled, or reused in a further process.

It will be understood that the compounds of formula (I) of the present invention may be prepared by the same methods which are used to prepare the composition of the present invention. Accordingly, the present invention provides for subsequent distillation of the compounds of formula (I) where m=1, 2, 3, 4, or 5. Distillation techniques for separating closely boiling fractions, either by atmospheric or reduced pressure techniques, including spinning band distillation and fractional distillation, can be used in isolating the compounds of formula (I). Other techniques for isolating compounds of formula (I) would be known to those skilled in the art.

According to the present invention, the levels of compounds where n=0 and/or n=1 in the final composition can be varied by distillation techniques to achieve the desired flash point. For instance, the present invention allows for variation in the amount of the parent secondary alcohol to adjust the flash point of the composition to a desired level. As such the flammability or flash point of the compositions can be varied depending largely on the remaining amount of parent alcohol (n=0) left in the composition. In a preferred embodiment, the flash point of the composition is greater than or equal to 61° C. (as measured by the closed cup method defined in AS/NZS 2106.2) so as to allow classification of the composition as non flammable according to the definition of a flammable liquid described in the Australian Dangerous Goods Code. Through varying the level of the parent alcohol remaining in the compositions of the present invention one will be able to also vary the flash point to suit the storage, transport or use requirements for the compositions. Alternatively, as the compounds and compositions of the present invention are likely to be miscible with water, then one skilled in the art would understand that water could also be added to increase the flash point and therefore decrease flammability. For instance it has been found that the addition of about 10% wt of water to the composition of the present invention renders it essentially non-flammable below 100° C.

In the manufacture of the compounds and compositions of ethoxylates of the present invention, the reaction is facilitated by addition of acid or base catalyst.

Preferably, the base catalyst is derived from alkali and alkaline earth metals. Most preferably, the best catalyst is an alkaline metal hydroxide such as lithium, sodium or potassium. The most preferred is potassium hydroxide.

The ethoxylation process of the present invention may also be catalysed with the use of Lewis acids (for example, boron trifluoride, antimony pentachloride, tin (IV) chloride, or aluminium alkylates) or Bronsted acids (for example, p-toluene sulphonic acid, fluorosulfonic acid or perchloric acid). The most preferred Lewis acid is boron trifluoride used as the etherate, or as a complex preformed with the alcohol.

The most preferred base catalyst for preparing the compounds and compositions of the present invention is potassium hydroxide, with the most preferred catalyst being potassium hydroxide which has been dissolved in MIBC and dehydrated. Of the acid catalysts, boron trifluoride is the most preferred due to its ease of handling, availability and high rates of reaction. Narrow range ethoxylation catalysts (NRE's) are also a preferred group of catalysts that are neither acid nor base catalysts, but give a narrow molecular weight range of products. NRE catalysts are well known to those experienced in the art. Useful examples of NRE catalysts are taught in U.S. Pat. Nos. 4,967,016, 5,162,589, and 5,844,115, amongst others.

The reaction may be done in a single pot or a two step process. In a two step process, the base catalyst is added to the alcohol to initially prepare an alkoxide ion. Accordingly, when the catalyst is potassium hydroxide and the secondary alcohol is MIBC, the alkoxide ion is potassium 4-methyl-2-pentoxide. It will be appreciated that water produced as a by-product from this initial reaction can be distilled off (removed) prior to the addition of EO.

In another embodiment, the EO may initially be reacted with an acid catalyst which activates EO to nucleophilic attack.

It is emphasised however that the preferred method for preparing the compositions and compounds of the present invention is performed in a single pot or in a continuous process. The most preferred method for preparing the compositions and compounds of the present invention is a continuous process. In a continuous operation, a small amount of EO is added to catalysed MIBC and reacted out. The product is then distilled to recover most of the unreacted MIBC, which is then recycled. The product is then collected as is, or is further distilled to recover the product and leave a residue containing catalyst, PEG's and highly built MIBC ethoxylates. Continuous plant processes suitable for carrying out this are known, and are commercially available. A typical version comprises a long heated pipe in which the alcohol flows as it is being reacted. To save space, such reactors are often bent back on themselves in a series of S's, and are often referred to as Serpentine reactors.

The compounds and compositions of the present invention can be used as a frothing agent in existing froth flotation processes. They can be used as replacements for existing frothers or to supplement frothers currently used. An example of how the present composition and compounds of the present invention can be used as a frother in a typical mineral or coal flotation plant process is as follows:

1. The frother is typically added to either a conditioning vessel prior to flotation or to the first flotation cell directly, depending on the amount of time and agitation required to disperse the product in the mineral/coal slurry. In the case of Jameson® cells the frother is added to the downcomer portion of the cell to optimise dispersion within the high shear environment typical of this type of cell. Other reagents such as collectors and dispersants may be added at the same time.

2. Once in the flotation cells the frother acts to facilitate the generation of a stabilised froth to aid in the recovery of fine particles. The desired mineral or coal particles are concentrated through attachment of these particles to the stable air bubbles which rise to the top of the cell. Other reagents at this point will assist with selective collection of the desired minerals, and depression of unwanted gangues or other minerals.

3. The mineral/coal enriched froth concentrate is then collected from the top of the cell either passively by over spilling into collection launders or by mechanical skimming.

4. The mineral/coal enriched concentrate may then be subjected to further flotation cleaning to further enhance the selectivity of desired mineral/coal. Further flotation may or may not require additional frother dosing.

5. The final concentrate is typically collected and thickened/dried before further processing.

The preferred compounds and compositions of the present invention facilitate the formation and stabilisation of fine bubbles under high shear conditions in a manner very similar to the parent alcohol, MIBC, despite the addition of the glycol ether units. This is a desirable property of MIBC that has led to it being the frother of choice in many operations up to the present day, despite its flammability, toxicity and odour. The preferred compounds and compositions of the present invention are therefore a major contribution to the practice of flotation. The preferred compositions also generally yield a "brittle" froth on the surface of the liquor similar to that formed by MIBC alone, and that is believed to contribute to both selectivity and ease of operation in the separation of desirable products during flotation.

It will be appreciated that although the preferred use of the present invention is as a frother in mineral flotation, the compounds and compositions thereof may also be applicable to other uses which currently utilises $C_3$-$C_9$ alcohols. For instance, the ethoxylated products of the present invention may find use as surfactants in hydraulic fluids. The products act as surfactants or "coupling agents". Coupling agents are compounds or compositions with properties intermediate between or combining the characteristics of solvents and of surfactants and work to compatibilise otherwise incompatible liquids. The surface active nature and molecular structure of the product is such that it may assist in the formation of micelles to provide emulsion stability and other desirable properties, along with the use of other chemicals such as corrosion inhibitors or lubricants, for example, as taught in U.S. Pat. No. 6,558,569.

Because of the small but significant improvement in solvency and surfactant properties when only a small number of ethylene oxide units are added to MIBC, the preferred products of the present invention can be used with advantage in many of those specific applications where MIBC is currently used. For example, MIBC is used as a solvent/co-solvent for the formulation of dyes, oils, resins and other industrial, pharmaceutical or agrochemical products. For example, the preferred compounds and composition of the present invention may also be used with surfactants to compatibilise essential oils, perfumes, mineral oils and other organic compounds (in particular, hydrocarbon liquids) with polar compounds, preferably organic compounds like alcohols, as well as water, etc., and mixtures thereof to formulate domestic and industrial cleaners and disinfectants, as well as agricultural and veterinary products. As the Flash Point and other OH&S properties of the preferred composition of the present invention are desired over the pure parent alcohols this makes them more suitable for many of the current applications where the use of the parent alcohols may be restricted because of flammability or toxicity. In these applications it may be preferred to use compositions essentially free of MIBC.

EXAMPLES

Example 1

MIBC was charged to an autoclave with potassium hydroxide (KOH) as catalyst. The charge was heated to 160° C. under stirring and ethylene oxide added slowly. Reaction progress was monitored by observing the rise and fall in pressure as EO was added and reacted, and the rise in temperature due to reaction. If the absolute pressure rose above 200 kPa, EO addition was stopped until if fell below 200 kPa again.

Product was fractionally distilled to selectively remove all of the free, unreacted MIBC. Distillation was carried out at atmospheric pressure where the boiling point of MIBC is 132° C. A controlled amount of fresh MIBC was then added back.

Product was analysed by gas chromatography as made and then again after distillation and after addition of the free MIBC. Pensky-Martens Closed Cup flash point was measured by standard methods. The froth properties of the products were assessed by two phase flotation tests in a 2 litre laboratory Agitair flotation cell. The main observations made were froth structure and stability and volume of froth generated under standard conditions. These were compared to results using MIBC.

The product was not neutralised, and was a light teak colour due to the decomposition of minor impurities (<1% by mass) in the feed material.

Detailed conditions and results for four runs are given below in Table 1.

Example 2

MIBC was charged to an autoclave and Boron Trifluoride Etherate $BF_3.OEt_2$ added as catalyst. The charge was heated to 100° C. under stirring and EO added and reacted. Due to the different selectivity of the $BF_3$ catalyst, a far higher ratio of EO could be added to the alcohol, but excess alcohol still needed to be removed by distillation.

The product was distilled under vacuum (water pump vacuum, ~15 mm Hg) in a rotary film evaporator at 90° C. Under these conditions some of the MIBC mono-ethoxylate is removed along with the free MIBC, but the residual free MIBC can be controlled by the distillation temperature.

The product was analysed for Pensky-Martens Closed Cup flash point, and for composition by gas chromatography. Laboratory froth performance was also assessed as before.

TABLE 1

| | Run: | | | | | | | | | | | |
|---|---|---|---|---|---|---|---|---|---|---|---|---|
| | 1 | 2 | 3 | 4 | 1 | 2 | 3 | 4 | 1 | 2 | 3 | 4 |
| | Catalyst | | | | | | | | | | | |
| | aq KOH | solid KOH | aq KOH | aq KOH | KOH | KOH | KOH | KOH | KOH | KOH | KOH | KOH |
| | Loading | | | | | | | | | | | |
| | 1,000 | 1,000 | 1,000 | 250 | 1,000 | 1,000 | 1,000 | 250 | 1,000 | 1,000 | 1,000 | 250 |
| | EO/Kg | | | | | | | | | | | |
| | 32 | 32 | 52 | 29 | 32 | 32 | 52 | 29 | 32 | 32 | 52 | 29 |
| MIBC+ | before distillation | | | | after distillation | | | | after MIBC back addn | | | |
| 0 EO | 93.00 | 91.25 | 89.50 | 91.19 | 0.00 | 0.00 | ~ | 0.00 | 8.50 | 8.50 | 8.50 | 8.50 |
| 1 EO | 3.94 | 4.67 | 5.20 | 4.61 | 56.28 | 56.15 | 49.51 | 56.08 | 51.49 | 51.13 | 45.30 | 51.06 |
| 2 EO | 1.57 | 1.73 | 2.65 | 1.72 | 22.37 | 20.75 | 25.28 | 20.90 | 20.47 | 18.89 | 23.13 | 19.03 |
| 3 EO | 0.68 | 0.73 | 1.10 | 0.70 | 9.66 | 8.77 | 10.49 | 8.52 | 8.84 | 7.99 | 9.60 | 7.76 |
| 4 EO | 0.32 | 0.33 | 0.55 | 0.31 | 4.61 | 3.97 | 5.26 | 3.81 | 4.22 | 3.61 | 4.82 | 3.47 |
| 5 EO | 0.19 | 0.18 | 0.33 | 0.17 | 2.66 | 2.20 | 3.17 | 2.11 | 2.43 | 2.01 | 2.90 | 1.92 |
| 6 EO | 0.12 | 0.11 | 0.22 | 0.10 | 1.66 | 1.28 | 2.09 | 1.26 | 1.52 | 1.17 | 1.91 | 1.15 |
| 7 EO | 0.08 | 0.08 | 0.17 | 0.08 | 1.18 | 0.92 | 1.58 | 0.91 | 1.08 | 0.84 | 1.45 | 0.83 |
| 8 EO | 0.06 | 0.05 | 0.13 | 0.06 | 0.80 | 0.60 | 1.21 | 0.67 | 0.73 | 0.55 | 1.11 | 0.61 |
| 9 EO | 0.04 | 0.03 | 0.10 | 0.04 | 0.54 | 0.36 | 0.92 | 0.49 | 0.49 | 0.33 | 0.85 | 0.44 |
| 10 EO | 0.02 | 0.00 | 0.05 | 0.02 | 0.24 | 0.00 | 0.49 | 0.24 | 0.22 | 0.00 | 0.44 | 0.22 |
| Other[1] | | 0.89 | | 1.10 | | 5.44 | | 5.38 | | 4.98 | | 4.92 |
| BR[2] | | | | | 1.600 | 1.536 | 1.730 | 1.542 | 1.400 | 1.320 | 1.560 | 1.325 |
| ratio[3] | 18.2% | 16.6% | 21.1% | 16.0% | 18.2% | 16.6% | 21.1% | 16.0% | 18.2% | 16.6% | 21.1% | 16.0% |
| n > 4[4] | | | | | 7.0% | 5.4% | 9.5% | 5.7% | 6.5% | 4.9% | 8.7% | 5.2% |
| Flash Pt[5] | | | | | | | | | 69EC | 69EC | 69EC | 69EC |

Notes:
[1] Other. Unidentified peaks, including Poly Ethylene Glycols (PEG's).
[2] BR = Build Ratio. Total moles of EO in MIBC ethoxylates over total moles of MIBC as free alcohol and as ethoxylates.
[3] ratio = A measure of tailing of the product distribution, calculated as (M3 + M4)(M1 + M2), where Mn is the wt % of the MIBC ethoxylate with n EO residues.
[4] n > 4. A measure of tailing of the product distribution, calculated as the total wt % of all MIBC ethoxylate with more than 4 EO residues as a fraction of all MIBC and MIBC ethoxylate species present.
[5] Flash Pt. Pensky-Martens Closed Cup flash point as measured by standard methods.

Detailed conditions and results for two runs are given below in Table 2.

TABLE 2

| | Run: | |
|---|---|---|
| | 1 | 2 |
| Catalyst | BF$_3$ | BF$_3$ |
| Loading | | |
| EO/Kg | 2,300 | 2,300 |
| MIBC+ | 540 vacuum distilled | 540 |
| 0 EO | 7.32 | 5.28 |
| 1 EO | 28.93 | 29.43 |
| 2 EO | 28.45 | 29.31 |
| 3 EO | 18.25 | 18.69 |
| 4 EO | 9.24 | 9.45 |
| 5 EO | 3.80 | 3.88 |
| 6 EO | 1.35 | 1.34 |
| 7 EO | 0.41 | 0.40 |
| 8 EO | 0.08 | 0.00 |
| 9 EO | 0.00 | 0.00 |
| 10 EO | 0.00 | 0.00 |
| Other[1] | | |
| BR[2] | 1.74 | 1.81 |
| ratio[3] | | |
| n > 4[4] | 5.6% | 5.6% |
| Flash Pt[5] | 71EC | 74EC |

Notes:
[1] Other, Unidentified peaks, including Poly Ethylene Glycols (PEG's).
[2] BR = Build Ratio. Total moles of EO in MIBC ethoxylates over total moles of MIBC as free alcohol and as ethoxylates.
[3] ratio = A measure of tailing of the product distribution, calculated as (M3 + M4)(M1 + M2), where Mn is the wt % of the MIBC ethoxylate with n EO residues.
[4] n > 4. A measure of tailing of the product distribution, calculated as the total wt % of all MIBC ethoxylate with more than 4 EO residues as a fraction of all MIBC and MIBC ethoxylate species present.
[5] Flash Pt. Pensky-Martens Closed Cup flash point as measured by standard methods.

Examples 3 to 8

MIBC was ethoxylated in a continuous reactor and the product continuously distilled to remove excess free alcohol. This was recycled to the reactor feed. The conditions were as follows.

| | |
|---|---|
| Inlet Temperature | 184° C. |
| Catalyst | Aqueous KOH (50% w/w solution) |
| Catalyst level | Approximately 400 ppm on feed alcohol |
| Contact time | 2 hours |
| Ethylene Oxide (EO) | Various (Table 3) |

EO was added at a set ratio to the feed alcohol. However, this set ratio was increased from time to time over the course of the run, to determine the impact on product distribution and properties. The feed ratios and the consequential ethoxylate distributions are given in Table 3. These distributions are determined by gas chromatography, using uncorrected peak areas.

TABLE 3

| | Example | | | | | |
|---|---|---|---|---|---|---|
| | 3 | 4 | 5 | 6 | 7 | 8 |
| EO ratio | 0.06 | 0.07 | 0.08 | 0.11 | 0.13 | 0.14 |
| BR | 1.28 | 1.37 | 1.40 | 1.52 | 1.61 | 1.69 |
| HR[1] | 0.10 | 0.13 | 0.15 | 0.18 | 0.22 | 0.25 |
| 0 EO | 0.06 | 0.07 | 0.08 | 0.11 | 0.13 | 0.14 |
| 1 EO | 3.80 | 5.29 | 5.81 | 4.57 | 5.19 | 4.23 |
| 2 EO | 57.42 | 55.42 | 54.56 | 49.02 | 47.28 | 46.51 |
| 3 EO | 14.62 | 16.22 | 17.31 | 18.03 | 19.97 | 20.95 |
| 4 EO | 5.06 | 6.43 | 7.21 | 7.91 | 9.67 | 10.62 |
| 5 EO | 2.27 | 3.16 | 3.60 | 4.01 | 5.35 | 6.00 |
| 6 EO | 1.30 | 2.05 | 2.31 | 2.66 | 3.63 | 4.10 |
| 7 EO | 0.87 | 1.56 | 1.87 | 2.29 | 2.80 | 3.10 |
| 8 EO | 0.69 | 1.40 | 1.64 | 2.07 | 2.54 | 2.66 |

[1] HR = Heavies Ratio. The ratio between the combined areas of the 3$^{rd}$ and 4$^{th}$ ethoxylate peaks divided by the combined areas of the 1$^{st}$ and 2$^{nd}$ peaks.

The products from Examples 3 to 8 were combined. The Heavies Ratio of this combined product was 0.24.

Acetic acid was added at a low level to neutralise the catalyst residues.

Free MIBC was added to the combined product to bring the final free alcohol level up to 7.5% by weight. This was the level determined by Pensky-Marten Closed Cup flash point method to give a Flash Point of 72° C.

Water was also added to the combined product at a rate of 15 wt %.

This combined and adjusted product from Examples 3 to 8, which will be referred to hereinafter as "Batch 1", was submitted for field trialing in a number of flotation applications.

Examples 9 to 11 and Comparative Examples 1 to 3

In the three comparative examples, MIBC was dosed at 250 mL/min into the suction side of the flotation pump located at the base of the feed sump to the Jameson® Cell. Diesel was dosed at approximately the same dose rate into the flotation feed prior to the Jameson® Cell.

In Examples 9 and 10, the product described as Batch 1 was added in place of MIBC at the same dose rate. Allowing for the 15% water in Batch 1, this means that the dose was effectively only 212 mL/min. All other conditions were left unaltered, apart from the natural variation in ash content that occurred in the feed to the plant. With such a high quality coal, however, these small changes in feed ash can affect the performance of the flotation drastically.

These results are summarised in Table 4 below.

TABLE 4

| | Feed Ash (%) | Product Ash (%) | Tailings Ash (%) | Yield (%) | Combustible Recovery (%) | Reagent | Dose Rate (mL/min) |
|---|---|---|---|---|---|---|---|
| Comparative Example | | | | | | | |
| 1 | 16.3 | 5.8 | 22.3 | 36.9 | 41.4 | MIBC | 240 |
| 2 | 12.6 | 5.2 | 23.4 | 59.2 | 64.2 | MIBC | 250 |
| 3 | 17.2 | 8.6 | 33.7 | 65.7 | 72.5 | MIBC | 300 |

TABLE 4-continued

| | Feed Ash (%) | Product Ash (%) | Tailings Ash (%) | Yield (%) | Combustible Recovery (%) | Reagent | Dose Rate (mL/min) |
|---|---|---|---|---|---|---|---|
| Example | | | | | | | |
| 9 | 15.2 | 5.6 | 21.6 | 39.9 | 44.4 | Batch 1 | 250 |
| 10 | 17.6 | 6.5 | 32.8 | 57.8 | 65.6 | Batch 1 | 300 |
| 11 | 18.0 | 7.3 | 32.8 | 58.2 | 65.8 | Batch 1/ MIBC | 125/125 |

During the test period, it was observed that when dosing the Batch 1 product a much finer bubble was obtained than for the equivalent dose rate of MIBC. This would indicate that further recovery can be achieved with the same air volume due to the increase in surface area available for the attachment of coal to an air bubble. This was observed in all three examples.

Example 12

A preliminary trial using Batch 1 product was carried out in the Microcel® to look at the cell operability and to determine suitable dose rates. The coal treated was similar to that used in Examples 9 to 11. It was noted during the trials that the bubble size decreased dramatically, as was observed in the Jameson® Cell. This testwork indicated that a dramatic improvement in coal recovery was made when dosing the Batch 1 product.

Example 13

Batch 1 product was trialed in an EKOF® cell being used in the full scale washing of coal, against the commercial frother in use at the time, Batch 1 product could be dosed at half the rate with no observable detrimental affect on the process. An additional benefit was a reduction in foaming around the plant. A build up of solid coal laden foam on the product thickeners which formed during operation with the competitive frother disappeared after two days of running with Batch 1 product.

Example 14

Batch 1-product was evaluated on a commercial lead/zinc plant against MIBC, the incumbent frother. Preliminary evaluation demonstrated that Batch 1 product performed at least as well as MIBC both metallurgically and from a circuit stability perspective. Frother consumption was 33% of that of MIBC.

Example 15

In another experiment, ore from another commercial lead/zinc operation was treated in a laboratory scale flotation cell, comparing the performance of MIBC with Batch 1 product. The results indicated that the sample of the ethoxylate of the present invention performed equal to, or in some cases, exceeded the results achieved using MIBC. A summary of test conducted and results are presented in Table 5.

TABLE 5

| Test | Description | Dose Rate | Recovery Lead | Recovery Zinc | Grade Lead | Grade Zinc |
|---|---|---|---|---|---|---|
| A | MIBC at standard dose rate | 60 g/t | 82.8 | 93.3 | 73.8 | 40.1 |
| B | Invention sample at MIBC dose rate | 60 g/t | 81.3 | 92.1 | 68.0 | 43.6 |
| C | Invention sample at 50% MIBC Dose | 30 g/t | 83.0 | 91.0 | 71.5 | 45.5 |

This product was submitted for preliminary screening as a frother in coal washing, and in sulphide mineral flotation. Results suggest that the product is at least comparable to MIBC in flotation performance.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The claims defining the invention are as follows:

1. A composition comprising at least two compounds of formula (II):

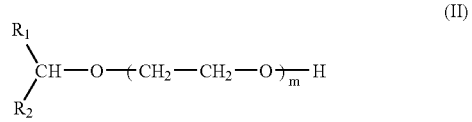

wherein $R_1$ and $R_2$ are each independently $C_1$-$C_4$ alkyl, and n is an integer $\geq 0$ and wherein the average molar value of n for the total of the compounds of formula (II) in said composition is in the range of 1 to 2.

2. A composition according to claim 1 wherein the average molar value of n is about 1.7.

3. A composition according to claim 1 wherein $R_1R_2CH-$ is 4-methyl-pent-2-yl.

4. A composition according to claim 1, wherein the compound of formula (II) where n=0 comprises less than 15% by weight of the total composition.

5. A composition according to claim 1, wherein the compound of formula (II) where n=0 comprises less than 10% by weight of the total composition.

6. A composition according to claim 1, wherein the compound of formula (II) where n=0 comprises less than or equal to 6.5% by weight of the total composition.

7. A composition according to claim 1, wherein the total combined weight of compounds where n=0 and n=1 is such that the closed-cup flash point of said composition is greater than 65° C.

8. A composition according to claim 1, wherein the total weight of compounds of formula (II) where n is greater than 4 is less than 20% of the combined total of compounds of formula (II).

9. A composition according to claim 1 which further comprises other additives.

10. A method of preparing a composition comprising at least two compounds of formula (II):

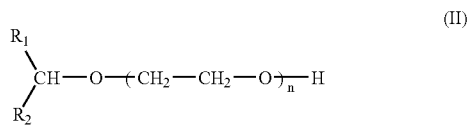

(II)

wherein $R_1$ and $R_2$ are each independently $C_1$-$C_4$ alkyl, and n is an integer $\geq 0$, and wherein the average molar value of n for the total of the compounds of formula (II) in said composition is in the range of 1 to 2, said method comprising:

reacting an excess of $C_3C_9$ secondary alcohol with ethylene oxide in the presence of a catalyst in an ethoxylation vessel to form a mixture of two or more compounds of formula (II), separating at least a portion of unreacted secondary alcohol from the mixture, and recycling the unreacted secondary alcohol back to the ethoxylation vessel.

11. A method according to claim 10, wherein the $C_3$-$C_9$ secondary alcohol is 4-methyl-2-pentanol.

12. A method according to claim 10 wherein the unreacted secondary alcohol is removed by distillation to provide a composition comprising unreacted secondary alcohol in an amount of less than 15% by weight of the total composition.

13. A method according to claim 12, wherein unreacted secondary alcohol comprises less than 10% by weight of the total composition.

14. A method according to claim 12, wherein the unreacted secondary alcohol comprises less than or equal to 8% by weight of the total composition.

15. A method according to claim 10 comprising a distillation step to remove from the composition compounds of formula (II) wherein n=0 and n1 such that the closed-cup flash point of said composition is greater than 65° C.

16. A method according to claim 11 wherein total weight of compounds of formula (II) where n is greater than 4 in said composition is less than 20% of the combined total of the compounds of formula (II) in the composition.

17. A method according to claim 10, wherein the ethylene oxide to $C_3$-$C_9$ secondary alcohol ratio is kept below 70 wt % in said ethoxylation vessel.

18. A method according to claim 17, wherein the ratio is kept below 10 wt %.

19. A method according to claim 10, wherein the catalyst is an alkali metal or alkaline earth metal base catalyst or a Lewis or Bronsted acid catalyst.

20. A method according to claim 10, wherein the catalyst is a Narrow Range Ethoxylation catalyst.

21. A method according to claim 19, wherein the alkali metal catalyst is potassium hydroxide.

22. A froth flotation process for the recovery of clean coal from a slurry, the process comprising adding a composition according to claim 1 to the slurry.

23. A froth flotation process according to claim 22, wherein the froth flotation process is performed in a Microcel®.

24. A froth flotation process according to claim 22, wherein the froth flotation process is performed in a Jameson® cell.

25. A froth flotation process according to claim 22 wherein the froth flotation process is performed in an EKOF® cell.

26. A method for improving the performance of a dissolved air flotation process, the method comprising adding a composition according to claim 1 to lower the liquid surface tension of a slurry used in the process.

27. A flotation process for the recovery and concentration of desirable minerals or selective removal of undesirable minerals from a slurry, the process comprising adding a composition according to claim 1 to the slurry.

28. A flotation process for the recovery of sulphide minerals from a slurry, the process comprising adding a composition according to claim 1 to the slurry.

29. A froth flotation process for refining mineral or coal, the process comprising adding a composition according to claim 1 to a slurry of mineral or coal.

* * * * *

UNITED STATES PATENT AND TRADEMARK OFFICE
CERTIFICATE OF CORRECTION

PATENT NO. : 7,576,244 B2  Page 1 of 1
APPLICATION NO. : 10/538249
DATED : August 18, 2009
INVENTOR(S) : Leeming et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 757 days.

Signed and Sealed this

Seventh Day of September, 2010

David J. Kappos
*Director of the United States Patent and Trademark Office*